US008244656B2

(12) United States Patent
Petit (10) Patent No.: US 8,244,656 B2
(45) Date of Patent: Aug. 14, 2012

(54) SYSTEM AND METHOD FOR PREDICTING RARE EVENTS

(75) Inventor: Cecilia Anna Paulette Petit, Quakertown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 800 days.

(21) Appl. No.: 12/284,976

(22) Filed: Sep. 25, 2008

(65) Prior Publication Data

US 2010/0076917 A1 Mar. 25, 2010

(51) Int. Cl.
*G06F 17/00* (2006.01)

(52) U.S. Cl. .......................................... 706/45
(58) Field of Classification Search ................... 706/12, 706/45
See application file for complete search history.

(56) References Cited

U.S. PATENT DOCUMENTS

| | | | |
|---|---|---|---|
| 6,470,320 B1 | 10/2002 | Hildebrand et al. | |
| 6,533,724 B2 | 3/2003 | McNair | |
| 7,725,328 B1 * | 5/2010 | Sumner et al. ..................... | 705/2 |
| 2002/0019870 A1 * | 2/2002 | Chirashnya et al. .......... | 709/224 |
| 2002/0099686 A1 | 7/2002 | Schwartz et al. | |
| 2003/0101076 A1 | 5/2003 | Zaleski | |
| 2004/0015337 A1 | 1/2004 | Thomas et al. | |
| 2004/0078232 A1 | 4/2004 | Troiani | |
| 2004/0103001 A1 | 5/2004 | Mazar et al. | |
| 2004/0236188 A1 | 11/2004 | Hutchinson et al. | |
| 2005/0119534 A1 | 6/2005 | Trost et al. | |
| 2006/0025931 A1 | 2/2006 | Rosen et al. | |
| 2006/0173663 A1 | 8/2006 | Langheier et al. | |
| 2006/0224416 A1 | 10/2006 | Lloyd et al. | |
| 2009/0083203 A1 * | 3/2009 | Cho et al. ........................ | 706/21 |

OTHER PUBLICATIONS

Yan, et al., Research on Event Prediction in Time-Series Data, 2004, Proceedings of the Third International Conference on Machine Learning and Cybernetics, Shanghai, pp. 2874-2878.*
See et al., Some Initial Experiements with Neural Network Models of Flood Forecasting on the River Ouse, 1997, Proceedings of GeoComputation, pp. 1-8.*
Povinelli, et al; "Temporal Pattern Identification of Time Series Data Using Pattern Wavelets and Genetic Algorithms"; Artificial Nerual Networks in Engineering; 1998; XP-002551871.
Billisngsley, P.; "Statistical Methods in Markov Chains"; The Annals of Mathematical Statistics; vol. 32, No. 1; Mar. 1961; pp. 12-40; XP-002551872.
Quinlan, J.R.; "Induction of Decision Trees"; Machine Learning; vol. 1; pp. 81-106; Mar. 1986; XP-002551873.
Bailar, et al; "Medical Uses of Statistics"; 2nd Edition; Nejm Book, Boston USA; 1992; p. 164; XP-002551874.

* cited by examiner

*Primary Examiner* — David Vincent
(74) *Attorney, Agent, or Firm* — Willard Jones, II (57) ABSTRACT

Systems and methods are provided for predicting rare events, such as hospitalization events. Predictor sequences may be generated by example systems and methods. Further, the fitness of those sequences may be measured. Sequences may be refined and/or combined with other sequences to produce better sequences. Related sequences may have their relationship identified and associated with the respective sequences. Finally, the sequences may be used to create a predictive model designed to determine, based on a sequence of events related to a person, if a hospitalization event is likely to occur in a given timeframe. Other models may be constructed and used to predict other rare events, based on related event sequences.

22 Claims, 5 Drawing Sheets

SYSTEM AND METHOD FOR PREDICTING RARE EVENTS

BACKGROUND OF THE INVENTION

Predicting rare events is difficult to model using traditional techniques. Most traditional techniques require balanced datasets to produce an accurate model. In other words, the model construction technique requires approximately equal numbers of target events and non-target events. This is a problem for trying to predict rare events, where the target event does not occur as often as the non-target events. Other statistical models usually look for correlations between historical variables and the outcome. These models typically do not take into account the impact of the order in which the variable changes occur. Often times, the most relevant event for prediction is a rare event, and current modeling techniques have difficulty modeling such infrequent events.

BRIEF SUMMARY OF THE INVENTION

One example embodiment of the present invention may include an example method. The example method may postulate a plurality of predictor sequences, where each sequence includes a plurality of variables, where each variable has a value, where each variable has an associated range, and where the variable value falls within the range associated with that particular variable. Then, for each sequence, the example method may determine if the sequence has an adequate fitness. If the sequence does not have an adequate fitness, the example method may refine the sequence until the sequence has an adequate fitness. Finally, the example method may predict the occurrence of a rare event based at least in part on a model, where the model is constructed from the plurality of predictor sequences having adequate fitness.

Several alternative example embodiments are possible. For example, the rare event may be a hospitalization event. The sequence refining may include discarding the current sequence and starting over, or randomly adjusting some or all of the sequence. Refining the sequence may also include breeding the sequence with another sequence, which may include randomly combining the elements of the sequence with elements of the other sequence. An example of postulating a sequence may include, for each sequence, generating a random value for a variable, where the value is within a range associated with the variable. Also adding the variable to a sequence, and repeating the generating and repeating the adding for as many variables as needed. Further, the number of variables needed may be based on a random number generated within a range of possible numbers.

In addition to generating sequences, the example method may store each sequence in a predictor sequence library. The method may also determine if two or more sequences of the plurality of sequences are related, and if related, associate a rule based at least in part on the relation. Relations may include having similar fitness measurements, or having identical sequence variable values, except that one variable in one of the sequences differs from the other sequence. Related sequences may have an identical composition of variables, but be arranged in a different order for each sequence. Related sequences may also include one sequence predicting a first result, and another sequence predicting a second result, wherein the two sequences are identical except for the insertion or deletion of one or more variables. The first and second outcome may predict substantially similar results, or be related by predicting substantially opposite results.

One example embodiment of the present invention may include a system with a module that is configured to postulate a plurality of predictor sequences, where each sequence includes a plurality of variables, where each variable has a value, where each variable has an associated range, and where the variable value falls within the range associated with that particular variable. Further the module may be configured to determine, for each sequence of the plurality, if the sequence has an adequate fitness. The module may be configured to refine the sequence, if the sequence does not have an adequate fitness, until the sequence has adequate fitness. Also, the module may be configured to predict the occurrence of a rare event based at least in part on a model, where the model is constructed from the plurality of predictor sequences having adequate fitness.

One example embodiment of the present invention may include a computer-readable storage medium encoded with instructions configured to be executed by a processor, the instructions which, when executed by the processor, cause the performance of an example method. The example method may postulate a plurality of predictor sequences, where each sequence includes a plurality of variables, where each variable has a value, where each variable has an associated range, and where the variable value falls within the range associated with that particular variable. Then, for each sequence, the example method may determine if the sequence has an adequate fitness. If the sequence does not have an adequate fitness, the example method may refine the sequence until the sequence has an adequate fitness. Finally, the example method may predict the occurrence of a rare event based at least in part on a model, where the model is constructed from the plurality of predictor sequences having adequate fitness.

DETAILED DESCRIPTION OF THE INVENTION

Example systems and example methods are provided to predict rare events by analyzing not just the correlations between input variables and target variables, but the order or sequence in which those predictor events occur. Example systems and example methods of the present invention may use multiple types of model building in conjunction with each other or as alternative embodiments to build a more accurate predictor of rare events. One example embodiment which will be used to illustrate example methods and example systems, according to the present invention, may include predicting hospitalization events for a patient. Meaning, based on data and the sequence of events occurring with respect to a specific person, predicting the likelihood that that person will require hospitalization in any given timeframe. By inputting various patient related data, a model may be built to predict rare events, such as a hospitalization. These rare events may be of interest to the patients, their doctor, their insurance provider, or any number of other third parties.

Figure 1:
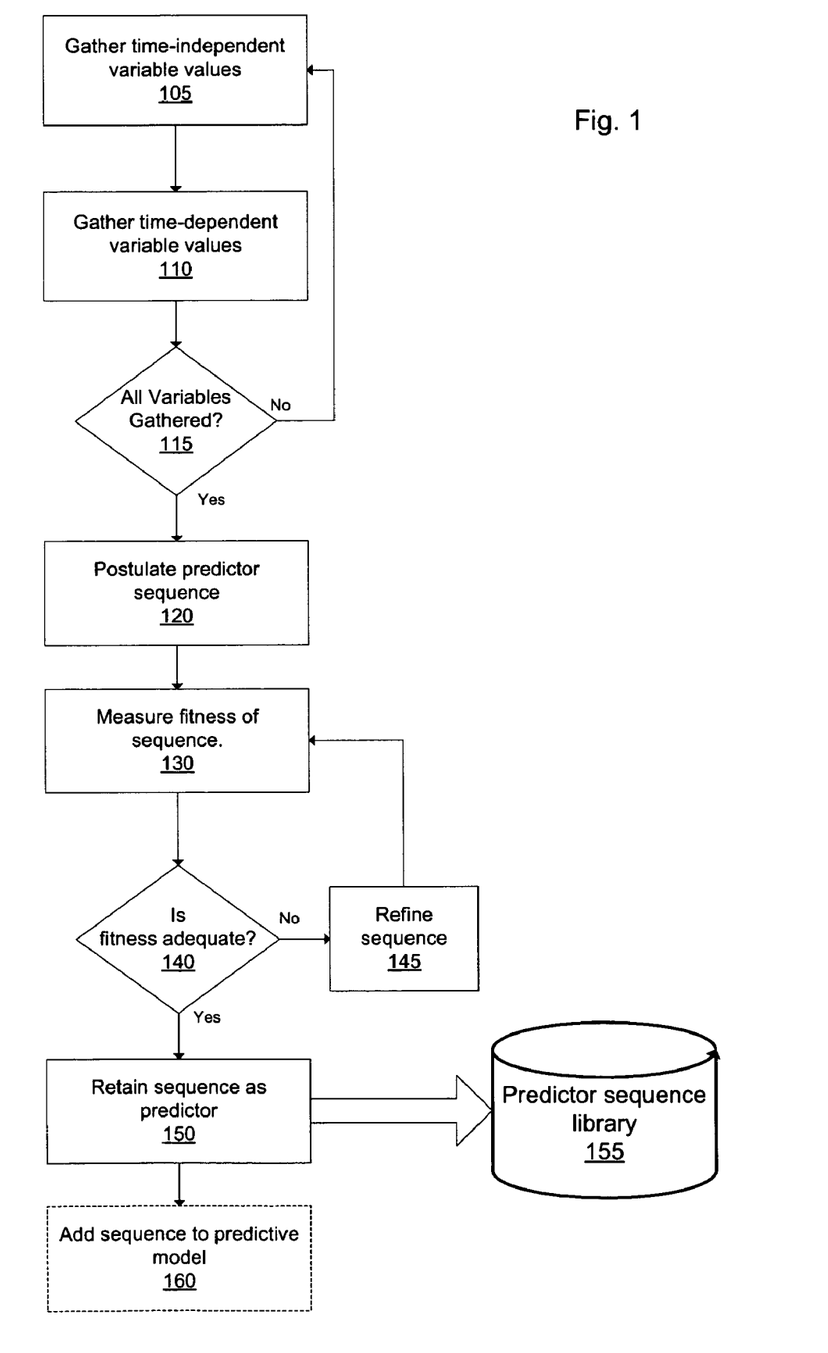
FIG. 1 illustrates an example procedure for postulating a predictor sequence, according to an example embodiment of the present invention.

One example procedure according to an example embodiment of the present invention is illustrated by FIG. 1. At 105, the example procedure may gather time-independent variable values. Examples of these values may include things that do not change, such as date of birth, height (after a certain age), ethnicity, gender, family history, etc. Variables that are likely to remain the same or semi-time-independent, but may change could be gathered at 105, 110, or both. Examples of these variables may include geography (e.g., place where the patient lives), family size including marital status, career field, education level. Most values may actually be changeable in theory, but many values will be essentially time-independent, or probably time-independent, where the probability depends on other factors such as age (e.g., family size of a 25 year old is more likely to increase than someone much older). At 110, the example procedure may gather time-dependent variable values. These variables may include medical charts, medical records, medical device data, lab data, weight gain/loss, prescription claims, insurance claims, physical activity levels, climate changes of the patient's location, and any number of other medical or health related metrics. At 115 the example procedure may proceed when all the relevant variables have been gathered, or loop back if more variables are needed. Alternative example embodiments may have a loop back at each of 105 and 110, may have additional variable acquisition steps, or may have a single step for all variable gathering. The embodiment of FIG. 1 is only illustrative, and 115 illustrates that in one embodiment all of the relevant variables are collected before proceeding.

At 120, the example procedure may postulate a predictor sequence. There are several ways to postulate predictor sequences. One example postulation may include first assigning a label (e.g., an ID number) to each variable (e.g., the variables gathered at 105 and 110). Next, a random number generator may be used to pick a number within a range of numbers associated with a particular variable. This could be repeated as many times as necessary until the predictor sequence is at a desired length. Other ways to postulate predictor sequences are possible. See, for example, FIG. 3. Predictor sequence events do not need to be evenly spaced in time. The "length" of a predictor sequence may refer to the length of time the sequence represented for a series of hypothetical events (e.g., predictor variables). Predictor sequences may have the same number of events with different temporal spacing, or may have a different number of events spanning the same length of time. Alternatively, predictor sequence "length" may refer to the number of events. Here still, the events may have different temporal spacing between each other, two sequences may have the same length (e.g., number of events) but different temporal spacing patters, or two sequences of the same length (e.g., number of events), but may have different time spans (e.g., from the first event to the last event). The specific implementation of these example embodiments or combinations of these example embodiments may depend on the rare event the model is predicting. Different example embodiments may have different temporal spacing patters between events and/or between different predictor sequences.

At 130, the example procedure may measure the fitness of the sequence postulated at 120. "Fitness" may generally be a measure of how well the sequence predicts the target event (e.g., hospitalization events). The most straight-forward way is to measure the correlation between the sequence and the target variable. Alternatively or additionally, fitness may be reported in a coincidence matrix, depending on whether the measured model is used by itself or in combination with other models or prediction methods.

At 140, the example procedure may determine if the fitness of the sequence is adequate. The adequacy level required of a sequence is completely up to the model user, depending on the prediction needs, and may be customized in any number of ways. For example, one model may concern itself with the accuracy of prediction, (e.g., the percent of correctly predicted outcomes). Whereas, a second model may concern itself primarily with only the number of false negatives (e.g., the number of times the model incorrectly predicts that the event will not occur). The latter case may be the preferred measure for the example embodiment of a model to predict hospitalization events for insurance companies. If the model incorrectly predicted a hospitalization event (e.g., a positive or affirmative outcome), then the consequences (e.g., did not actually have to pay claims) is less severe than the opposite. The opposite, e.g., the model incorrectly predicted no hospitalization event (e.g., a negative outcome) may cause the insurance company to have to pay substantial claims that were not expected. Thus, in some cases, false negatives or false positives may be more relevant to a user than total accuracy. However, some measures may include a mix of criteria, as one measure may be primary, but not the exclusively relevant measure. As in the example just outlined, though false negatives may be more detrimental than false positives, total accuracy is still relevant. A company who predicts false positives and false negatives (e.g., total accuracy) better than other companies, may be able to predict premiums better too. That company would then be able to under bid any company who believes they cannot afford such low premiums because they have so many erroneous positive predictions (e.g., hospitalization events) in their model.

If the fitness of a sequence is not adequate, the sequence may be refined at 145, and this may be repeated until a sequence of adequate fitness is produced. Refining the sequence may also occur in a number of ways. One way would be to simply discard the sequence and make a new one using the same or a different method as the one used to make the discarded sequence. Another example method for refining the sequence is to adjust smaller aspects of the sequence. For example, the example method may substitute one element of the sequence, rearrange two or more elements of the sequence, or add/remove one or more events/sub-sequences. After the sequence has been refined, the fitness may be measured again to determine adequacy. At 150, once the sequence has been determined to be adequate, it may be retained in a sequence predictor library or repository 155. Optionally, if a model is currently being built, the sequence may be added to the predictive model at 160. From the sequence postulated by the example procedure, or from a library of sequences collected and stored; one or more sequences may be used as input variables in building a statistical model (e.g., PCA/PLS, Mixed Models, Survival Analysis, Neural Networks, Monte Carlo Methods, etc) to predict rare events.

Figure 3:
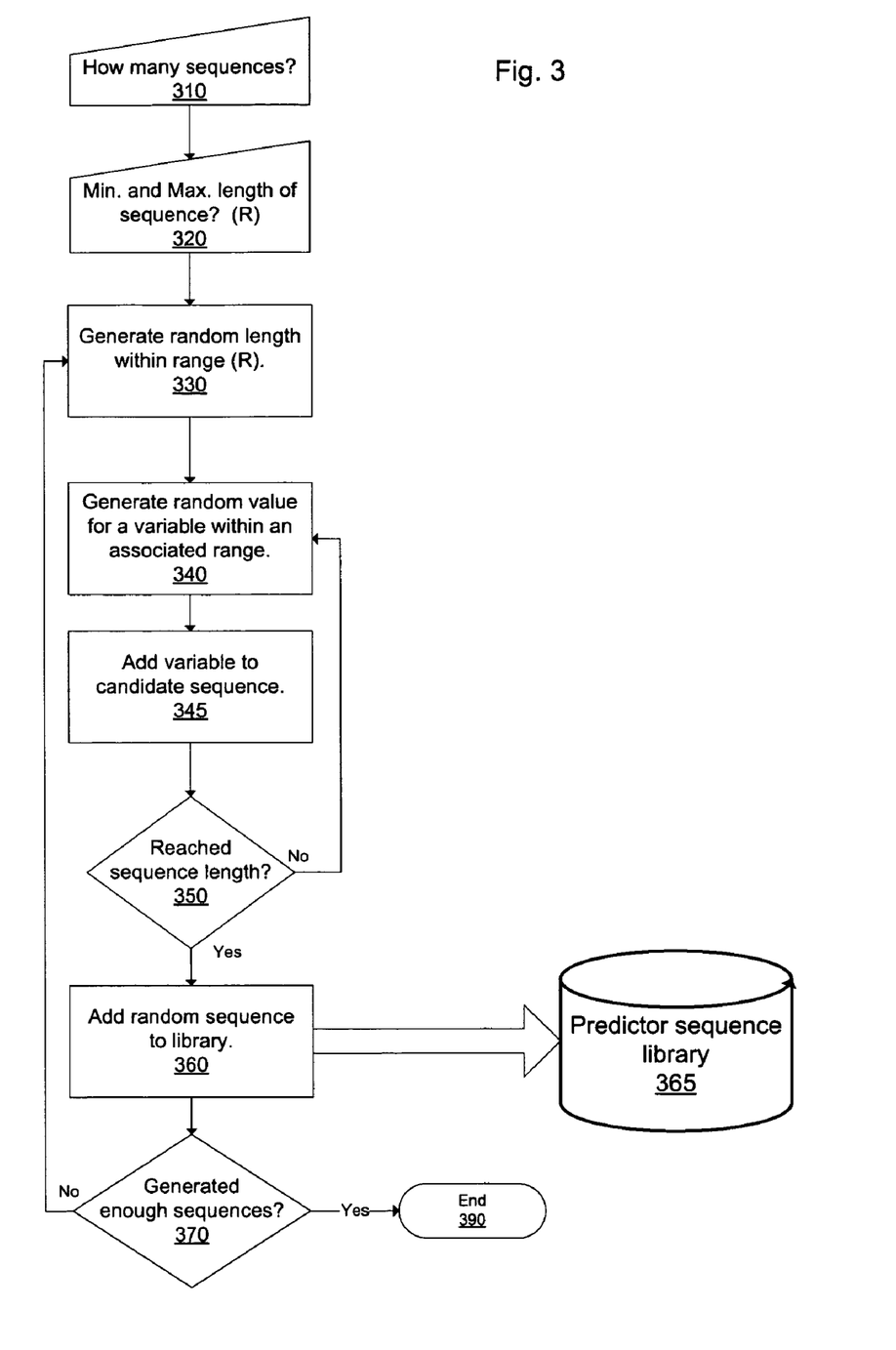
FIG. 3 illustrates an example procedure for generating predictor sequences, according to an example embodiment of the present invention.

FIG. 3 illustrates an example of how a library of predictor sequences may be generated. This method may be one example of how 120 may work, with the library size being 1 for a single sequence. The illustration assumes a user controlled method, but other embodiments may include fully automated or batch processing implementations. First, at 310, the user may be prompted for the number of sequences that should be created. Next, at 320, a range (e.g., "R") could be entered for the possible lengths of each sequence. For example, each sequence may be no less than 2 variables long, but no more than 10 variables long. At 330, a random number generator may generate a number within the range specified in 320. The library may also contain sequences of uniform length. If this is the case, then the minimum and maximum lengths specified for the range would be equal to each other and 330 would effectively only assign that number to the sequence.

Now, the actual variable generation may begin. At 340, a random value may be generated for a relevant variable. What variables are relevant may be specified by the user, imported from a preset package, or created any other way (e.g., 105-115). However, what variables are relevant to a target event will depend on any number of things, including what the target event is. Relevant example variables were listed above for an example target event of hospitalizations. Each variable will have an associated range (e.g., age from 0 to 100) or set of values (e.g., gender, either male or female). A random value from within the range of or set of values may be generated at 340, and at 345, that value may be added to the candidate sequence. At 350, the example procedure may return to generate another variable if the candidate sequence is not as long as specified by 330. Otherwise, at 360, the example procedure may add the completed sequence to a library, e.g., 365. If the number of sequences needed for the library have been created, then at 370, the example procedure may end. Otherwise, the example procedure may return to 330 to create another sequence.

Figure 2:
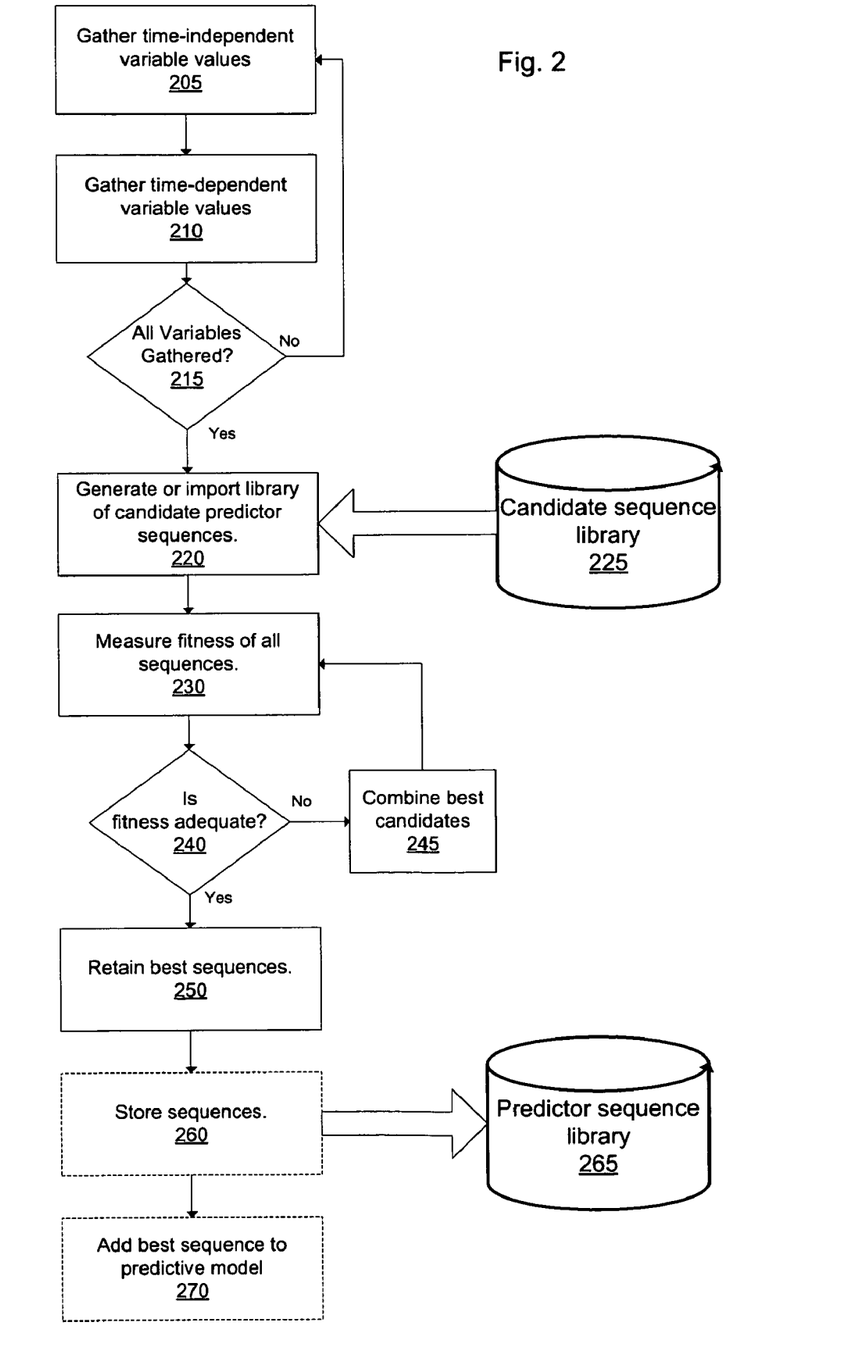
FIG. 2 illustrates an example procedure for breeding predictor sequences, according to an example embodiment of the present invention.

Another example procedure according to an example embodiment of the present invention is illustrated in FIG. 2. Here again, at 205, 210, and 215 the example procedures collects the various variable values until all of the relevant values have been collected. At 220 the example procedure may generate a library of candidate predictor sequences (e.g., in a similar way that FIG. 1 produced predictor sequences). 220 may alternatively import a library of candidate sequences form a repository 225. The example procedure may next measure the fitness of all the candidate sequences at 230.

At 240 a fitness check may be done. Here, the fitness of each sequence in the library or each generated sequence is checked. In this example method, it may be preferred to "grade" each sequence in the set, relative to each other or relative to some metric. If the fitness is found to not be adequate, the procedure may begin "breeding" a better predictive sequence by combining the best (e.g., top 5%) of the candidate sequences. Combinations may be created according to a set algorithm (e.g., the best and second best, etc., or the best and worst of the top 5%, etc.), or may be created by randomly combining the candidates. Adequacy of fitness could be defined in any number of ways. For example, a certain threshold may be set, such that a sequence is adequate when its prediction rate is more accurate than the minimum threshold. Alternatively, a set of sequences may simply be combined and recombined at 230 to 245 until the added accuracy resulting from the combination becomes negligibly small.

The actual combining of the two or more sequences could occur in a number of ways. One embodiment may combine the first half of one sequence and the second half of another sequence. Alternatively, smaller sections of each of two candidate sequences may be combined, or more candidates may be combined (e.g., four candidates each contributing a quarter of the length). Alternatively, random segments of two or more candidates may be chosen from each sequence to be assembled into the new combined sequence. After a new set of candidates has been made from the best of the prior set, again the example procedure may measure the fitness of the sequences at 230. This loop may repeat until an adequately fit set of sequences is created. At 250, the best or sufficiently adequate sequences may be retained. Optionally, the example procedure may store the retained sequences in a sequence library or repository (e.g., 265). Optionally, if a predictive model is currently being built, at 270, the example procedure may add the best sequence or sequences to the predictive model.

In another aspect and advantage of example embodiments of the present invention includes how sequence patterns are dealt with after being constructed. A more robust and flexible model may be created by taking into account that some sequences may not need to be identical to be essentially or effectively equivalent. For example, each sequence of a set of sequences (e.g. 230) may contain information or rules associated with them, relative to other possible configurations of the sequence. One example may include alternative events in a sequence position. For example, if a first sequence, A-K-C-D-E-F-G-H, and a second sequence, A-P-O-C-D-E-F-G-H produce the same fitness results for the target event prediction model, then a rule may be established that these are equivalent. Additionally, if it turns out that all sequences beginning with A- and ending with -C-D-E-F-G-H produce substantially similar fitness results, then the sequence set may be expressed with a wild card variable, such as A-*-C-D-E-F-G-H. Wild card variables may be limited to one or more variables. For example, a certain sequence of events (where each event is a variable with a value) may be unaffected by one variable regardless of that variable's value, but affected by a different variable. In this example, the wild card may not stand in for any variable of any value, but rather any value of certain variables. Structuring example embodiment of the present invention to recognize similar effective sequence combinations and/or to express sequences with wildcards allows for greater control and flexibility over the model creation and adjustment.

Another example may include switching the order of events. For example, A-B-C-D-E-F-G-H may have the same effective result at A-B-C-D-F-E-G-H. Another example may include omitting a sequence variable. For example, A-B-C-D-E-F-G-H may have the same effective result as A-B-C-E-F-G-H. It may not necessarily be the case that a change in sequence results in an essentially similar result. For example, it may be the case that whenever a chain of events A-B-C occurs, a certain result happens (e.g., high chance of target event occurring in the next month). However, it may also be the case that when some other event, Z, occurs between events B and C, e.g., A-B-Z-C, there is an opposite effect (e.g., low chance of target event occurring in the next month). When an alteration of a candidate sequence produces a substantially similar, but not necessarily identical outcome, the alteration may be noted as similar with an associated penalty. In this way, example embodiments have the flexibility to recognize a close but imperfect match that may not have otherwise been caught with a more rigid model if that exact alternative sequence was not included in the training set. However, if the alternative is recognized as a similar sequence with a penalty, the model may identify situations with this variable sequence and make an appropriate response with regard to the original sequence's fitness measurement and the alternative sequence's associated penalty.

Example embodiments of the present invention may assess not only the absolute fitness of a candidate sequence, but additionally, by assessing potential combinations, additions, and/or deletions of that sequence, and assessing how the fitness relates to the fitness of other sequences, rules may be established for the different sequence combinations. These rules may allow a far more flexible model for predicting the target event. Especially when modeling systems with a high degree of variable variation.

Figure 4:
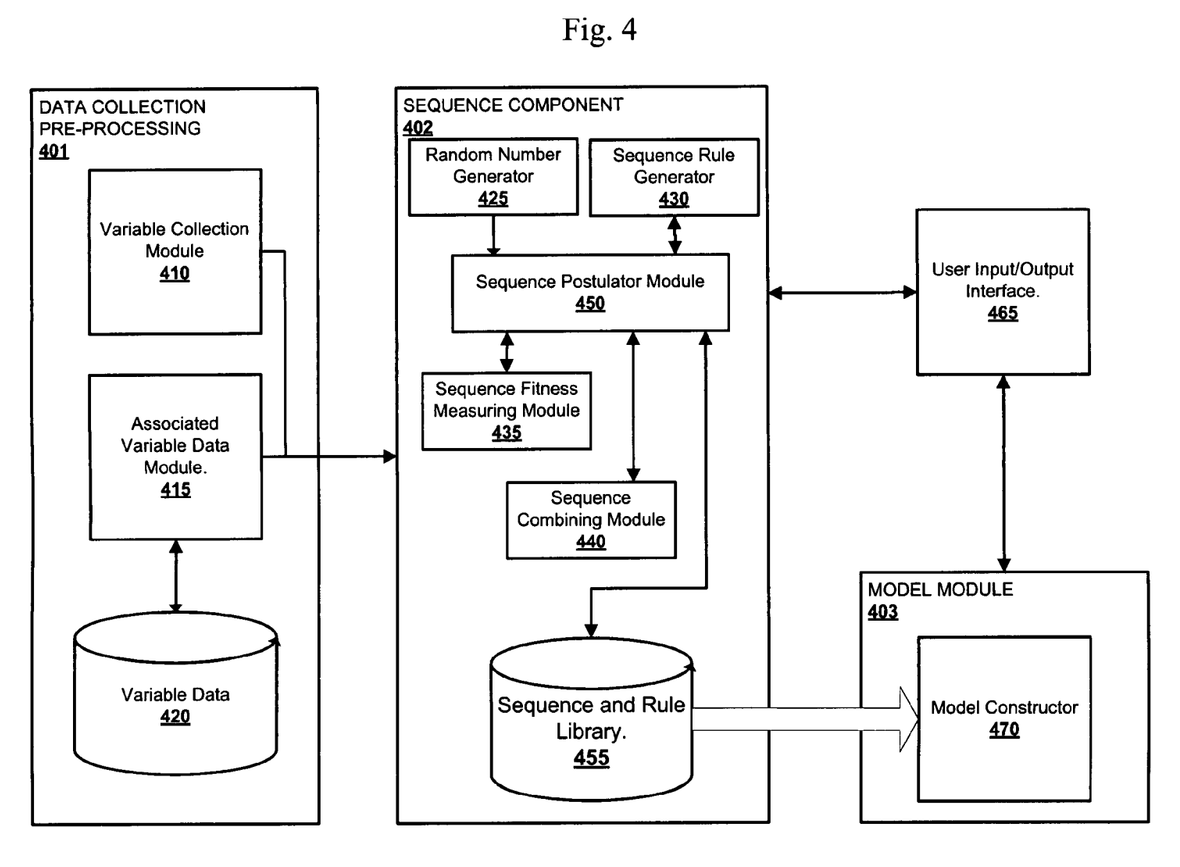
FIG. 4 illustrates an example device, according to an example embodiment of the present invention.

FIG. 4 illustrates an example system, according to an example embodiment of the present invention. The example system may include a data collection and pre-processing component 401. 401 may have a variable collection module 410, (e.g., configured to perform 105, 110, and/or 115). 401 may have an associated variable data module 415, which may be configured to determine and/or load certain characteristics of the variable. For example, 415 may determine the range or set of values a variable may be set to, e.g., 320 of FIG. 3. 401 may have an associated database 420 to store and retrieve variables and any associated variable data. The database may be located within the system or remotely via a connection (e.g., the Internet). Data collection pre-processing component 401 may interface or otherwise supply variable data to the sequence component 402.

Sequence component 402 may have a random number generator 425. 425 is shown supplying random numbers to the sequence postulator module 450. However, other components may also require random numbers (e.g., sequence combining module 440), and the illustration of FIG. 4 is not meant to restrict other example embodiments or implementations. The sequence postulator modules 450 may create the candidate sequences, e.g., 120 of FIG. 1. There may be a sequence fitness measuring module 435, configured to perform a function similar to what was described with respect to 130 and/or 230. There may be a sequence combining module 440 configured to perform the "breeding" of candidate sequences as described with regard to 245. There may be a sequence rule generator 430 configured to determine the similarity between sequence variations and/or alterations, and establish rules for those related sequences. Sequence component 402 may interface with a database or library 455 for storing the sequences and any associated rules. Database 455 may be the same physical repository as database 420 or a separate repository. Database 455 may also be located within the system, as shown, or connected remotely to the system. The Sequence Postulator Module 450 may be responsible, in connection with the interfaced modules, for generating one or more candidate sequence libraries 455. 455 may then supply a model constructor 470 of a model module 403 with sequences for a target event prediction model.

The system may also accept user input and/or deliver user output via a user I/O interface 465. Many other relevant components are possible in alternative example embodiments. Likely, many components common to computer systems will be included, such as processors, memory, servers, network connectors, etc. FIG. 4 is only one example illustrating example elements relevant to the current invention, and may not represent all the components known in the art to be associated with a computation system.

Figure 5:
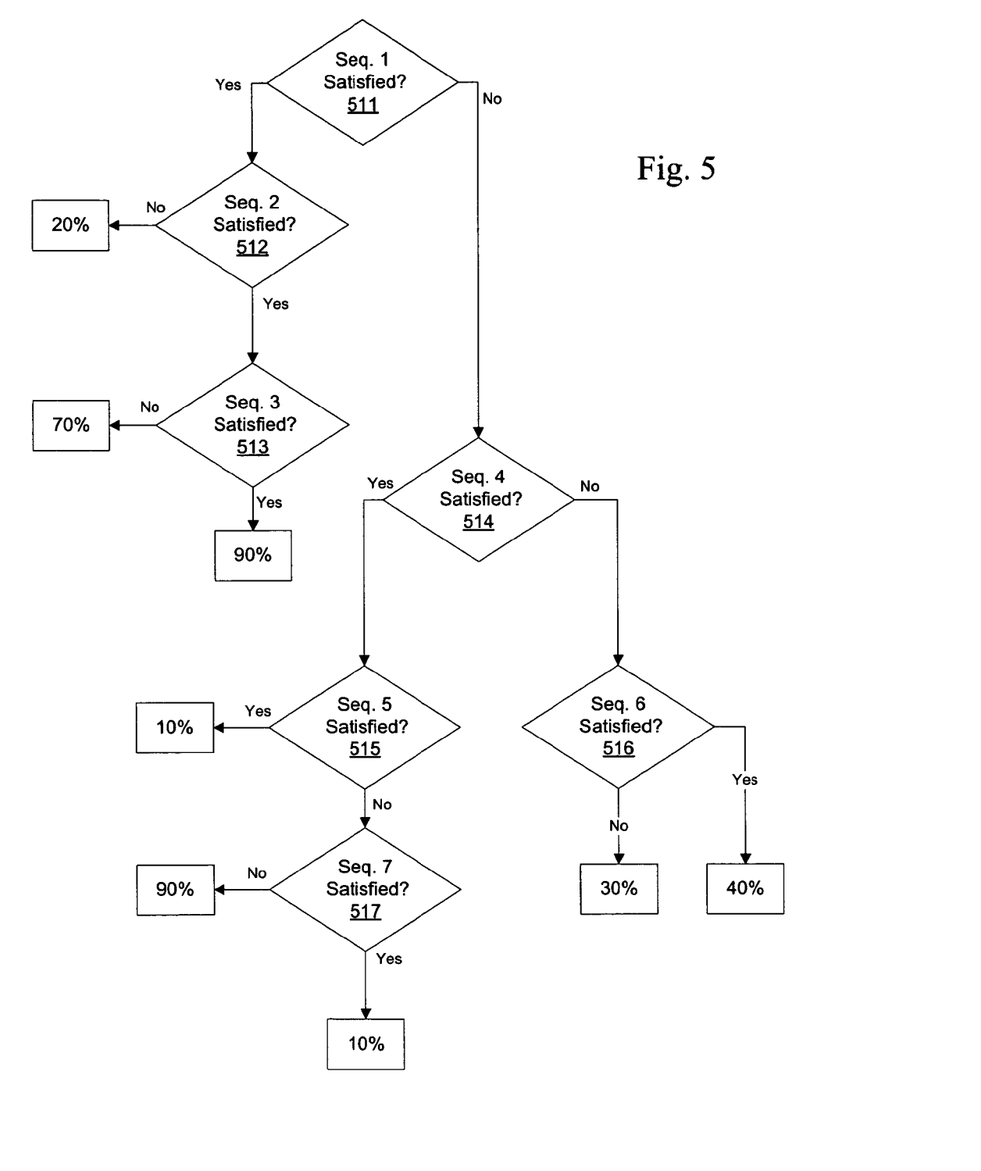
FIG. 5 illustrates an example Binary decision tree, according to an example embodiment of the present invention.

FIG. 5 illustrates an example embodiment of how a predictor sequence model may be built. Using the prediction rates ascertained during the predictor sequence creation and assessment, a model may be built of decision trees with nodes made up of predictor sequences, and leaves made up of probabilities. FIG. 5 illustrates one example tree, but a model may include any number of different dependent or independent trees.

As illustrated by the decision tree in FIG. 5, if sequence 1, sequence 2, and sequence 3 are all satisfied, then the probability of the relevant event occurring may be 90%. If sequence 1 is satisfied, sequence 2 is satisfied, but sequence 3 is not satisfied, then the probability of occurrence may be only 70%. It may also be seen that if sequence 1 is satisfied, but sequence 2 is not satisfied, then the probability of occurrence may be 20% regardless of the outcome of sequence 3. FIG. 5 shows an additional 5 leaf nodes, and respective sequence node patterns. The leaf nodes of FIG. 5 are only examples, leaf nodes could contain any probability value including 0% or 100%. The tree illustrated in FIG. 5 expressed probabilities as a series of AND functions and NOT functions. However, any other Boolean operator (e.g., OR, XOR, etc.) could be used in probability trees. An alternative embodiment may include a forest of trees, with one root node for every relevant starting sequence, and interdependent branches to subsequent sequence nodes, that collectively provide a leaf for every possible outcome of the prediction model. Other model structures are also possible, such as a relational database, a Neural Network, or a Monte Carlo method application. These modeling structures are known in the art, and may also be used as specific implementations in conjunction with the novel features of example embodiments of the present invention.

At this point, it may be appreciated how the model can be used to predict rare events. For example, there may be a binary tree (e.g., a plurality of binary decision trees similar to the tree illustrated in FIG. 5) with a root sequence, intermediate sequences, and leaf node probabilities. In an embodiment where the rare event to be predicted is hospitalizations, the health records and any other known information may be applied to the model. An example application of the model may compare sequence 1 to the information known about the patient to see if the sequence is satisfied. If the patient's information indicates the sequence is satisfied, then the example application may check for sequence 2 in the patient's information. If the patient's information indicates that sequence 2 is not satisfied, then the model may predict a 20% chance of a hospitalization event. Satisfying a sequence may mean an exact match, e.g., if sequence 1 consisted of A-B-C then the sequence of events A-B-C would have to be found in the patient's information to satisfy that sequence. Alternatively, as was described above, sequences may not need to be an exact match, e.g., if sequence 1 consisted of A-*-(C or D), then the sequence would be satisfied by A-W-C or A-F-D.

A hospitalization event is only one example of a rare event that may be predicted by models produced and run by example embodiments of the present invention. Any rare event and sequences of event leading up to the rare event may be modeled and predicted using example embodiments of the present invention. Example embodiments may predict when a production factory goes offline. Events may include: downtime per each piece of equipment, error messages per each piece of equipment, production output, employee vacations, employee sick days, experience of employees, weather, time of year, power outages, or any number of other metrics related to factory production capacity. Prediction sequences may be proposed, measured, and assimilated into a model. The model, comprising a plurality of sequences and respective outcome probabilities, may be used to compare to known data about events at a factory. The outcome of that comparison may lead to the probability the factory goes offline. It may be appreciated that any rare event and set of related events may be used in conjunction with example embodiments of the present invention to predict the probability of that rare event occurring.

The various systems described herein may each include a computer-readable storage component for storing machine-readable instructions for performing the various processes as described and illustrated. The storage component may be any type of machine readable medium (i.e., one capable of being read by a machine) such as hard drive memory, flash memory, floppy disk memory, optically-encoded memory (e.g., a compact disk, DVD-ROM, DVD±R, CD-ROM, CD±R, holographic disk), a thermomechanical memory (e.g., scanning-probe-based data-storage), or any type of machine readable (computer readable) storing medium. Each computer system may also include addressable memory (e.g., random access memory, cache memory) to store data and/or sets of instructions that may be included within, or be generated by, the machine-readable instructions when they are executed by a processor on the respective platform. The methods and systems described herein may also be implemented as machine-readable instructions stored on or embodied in any of the above-described storage mechanisms. The various communications and operations described herein may be performed using any encrypted or unencrypted channel, and storage mechanisms described herein may use any storage and/or encryption mechanism.

Although the present invention has been described with reference to particular examples and embodiments, it is understood that the present invention is not limited to those examples and embodiments. The present invention as claimed therefore includes variations from the specific examples and embodiments described herein, as will be apparent to one of skill in the art.

The invention claimed is:

1. A computer-implemented method for predicting rare events, comprising:
    postulating, by a computer processor, at least one predictor sequence, wherein each predictor sequence includes a plurality of variables, the postulating including:
        generating a random value for each variable, wherein the value is within a range associated with the variable;
        adding the variable to a predictor sequence; and
        repeating the generating and repeating the adding, until one of the following conditions is met:
            the plurality of variables represents a specified length of time and
            the plurality of variables represents a specified number of events;
    for each predictor sequence, determining, by the processor, if the predictor sequence has an adequate fitness, wherein fitness is measured by determining a correlation between the predictor sequence and a rare event to be predicted;
    if the predictor sequence does not have an adequate fitness, refining the predictor sequence until the predictor sequence has adequate fitness; and
    predicting the occurrence of the rare event based at least in part on a model, wherein the model is constructed from the at least one predictor sequence having adequate fitness.

2. The method of claim 1, wherein the rare event is a medical event.

3. The method of claim 1, wherein the rare event is a hospitalization event.

4. The method of claim 1, wherein the rare event includes at least one of the group: a machine, failure of equipment, and a plant failure.

5. The method of claim 1, wherein refining includes discarding the current predictor sequence and randomly generating values for a new predictor sequence.

6. The method of claim 1, wherein refining includes randomly adjusting at least one of a variable value and an order of the variables of the predictor sequence.

7. The method of claim 1, wherein refining includes breeding the predictor sequence with another predictor sequence, by randomly combining elements of the predictor sequence with elements of the another predictor sequence to produce a resulting sequence having the same size as the predictor sequence and the another predictor sequence.

8. The method of claim 1, wherein the specified length or specified number of events corresponding to the one of the conditions is a random number generated within a range of possible numbers.

9. The method of claim 8, wherein the range of possible numbers is received from user input.

10. The method of claim 1, further comprising:
    storing each predictor sequence in a predictor sequence library.

11. The method of claim 1, further comprising:
    postulating at least two predictor sequences;
    determining if two or more predictor sequences of the at least two predictor sequences are related, based on a comparison of fitness measurements of the at least two predictor sequences; and
    if related, associating, with each related predictor sequence, a rule describing the relation.

12. The method of claim 11, wherein two or more predictor sequences are related when the two or more predictor sequences have similar fitness measurements.

13. The method of claim 11, further comprising:
    determining whether two or more predictor sequences, which have identical predictor sequence variable values, except that one variable in one of the predictor sequences differs from the other predictor sequence, are related.

14. The method of claim 11, further comprising:
    determining whether two or more predictor sequences, which have an identical composition of variables, but being arranged in a different order for each predictor sequence, are related.

15. The method of claim 11, further comprising:
    determining whether two or more predictor sequences, which are identical except for the insertion or deletion of one or more variables, predict similar, but not identical results.

16. A system for predicting rare events, comprising:
    a module configured to postulate at least one predictor sequence, wherein each predictor sequence includes a plurality of variables, the postulating including:
        generating a random value for each variable, wherein the value is within a range associated with the variable;
        adding the variable to a predictor sequence; and
        repeating the generating and repeating the adding, until one of the following conditions is met:
            the plurality of variables represents a specified length of time and
            the plurality of variables represents a specified number of events;
    the module configured to determine, for each predictor sequence of the at least one predictor sequence, if the predictor sequence has an adequate fitness, wherein fitness is measured by determining a correlation between the predictor sequence and a rare event to be predicted;
    the module configured to refine the predictor sequence, if the predictor sequence does not have an adequate fitness, until the predictor sequence has adequate fitness; and
    the module configured to predict the occurrence of the rare event based at least in part on a model, wherein the model is constructed from the at least one predictor sequence having adequate fitness.

17. The system of claim 16, wherein the model is constructed by combining multiple predictor sequences using Boolean operators, thereby expressing a probability of an event as a Boolean expression that includes the combined predictor sequences, linked by the Boolean operators.

18. The system of claim 16, wherein the model is constructed by any one of the group including: building at least one decision tree having at least one predictor sequence as a node, and running at least one Monte Carlo method.

19. A computer-readable storage medium encoded with instructions configured to be executed by a processor, the instructions which, when executed by the processor, cause the performance of the following method:
postulating at least one predictor sequence, wherein each predictor sequence includes a plurality of variables, the postulating including:
generating a random value for each variable, wherein the value is within a range associated with the variable;
adding the variable to a predictor sequence; and
repeating the generating and repeating the adding, until one of the following conditions is met:
the plurality of variables represents a specified length of time and
the plurality of variables represents a specified number of events;
for each predictor sequence, determining if the predictor sequence has an adequate fitness, wherein fitness is measured by determining a correlation between the predictor sequence and a rare event to be predicted;
if the predictor sequence does not have an adequate fitness, refining the predictor sequence until the predictor sequence has adequate fitness; and
predicting the occurrence of the rare event based at least in part on a model, wherein the model is constructed from the at least one predictor sequences having adequate fitness.

20. The method of claim 1, wherein the correlation is measured as one of a percentage of correctly predicted outcomes, a number of false negatives, and a number of false positives.

21. The method of claim 11, further comprising:
identifying a variable contained in at least one, but not all predictor sequences in a set of two or more related predictor sequences; and
designating the identified variable as a wild card variable.

22. The method of claim 15, further comprising:
associating a penalty with the one or more variables that are inserted or deleted, relative to one of the two or more predictor sequences for which the one or more variables were not inserted or deleted.

* * * * *